(12) United States Patent
Clark et al.

(10) Patent No.: US 9,974,937 B2
(45) Date of Patent: May 22, 2018

(54) TEMPORARY TATTOO

(71) Applicant: Elyse Clark, Danbury, CT (US)

(72) Inventors: Elyse Clark, Danbury, CT (US); Mark G. Lang, Hewitt, NJ (US)

(*) Notice: Subject to any disclaimer, the term of this patent is extended or adjusted under 35 U.S.C. 154(b) by 0 days. days.

(21) Appl. No.: 15/360,124

(22) Filed: Nov. 23, 2016

(65) Prior Publication Data
US 2017/0143951 A1 May 25, 2017

Related U.S. Application Data

(60) Provisional application No. 62/259,286, filed on Nov. 24, 2015.

(51) Int. Cl.
A61M 37/00 (2006.01)
B44C 1/17 (2006.01)
B44C 3/00 (2006.01)

(52) U.S. Cl.
CPC ........ *A61M 37/0076* (2013.01); *B44C 1/1733* (2013.01); *B44C 1/1741* (2013.01); *B44C 1/1745* (2013.01); *B44C 3/005* (2013.01); *Y10T 428/24835* (2015.01)

(58) Field of Classification Search
CPC ....... B44C 1/17; B44C 1/1733; B44C 1/1741; B44C 1/1745; B44C 3/00; B44C 3/005; A61M 37/00; A61M 37/0076; A61M 37/005; Y10T 4228/24802; Y10T 4228/24835; Y10T 4228/2485; Y10T 4228/2486; Y10T 4228/24934; Y10T 428/24802; Y10T 428/24835; Y10T 428/24851; Y10T 428/2486; Y10T 428/24934
USPC ........... 428/195.1, 199, 201, 202, 211.1, 914
See application file for complete search history.

(56) References Cited

U.S. PATENT DOCUMENTS 5,942,065 A * 8/1999 Biggs et al. ............ B32B 31/00
156/90

* cited by examiner

*Primary Examiner* — Bruce H Hess
(74) *Attorney, Agent, or Firm* — Welsh Flaxman & Gitler LLC

(57) ABSTRACT

An image transfer sheet for producing a temporary tattoo having a base release sheet upon which a tattoo image is formed. The tattoo image comprising an image layer composed of a permanent adhesive and a water soluble adhesive having one or more inks integrated therewith. Wherein, after the tattoo image has been applied to a user and then subjected to water, the water soluble adhesive breaks apart and the permanent adhesive no longer has the ability to bond thereby allowing the tattoo image to easily be removed from the user.

10 Claims, 2 Drawing Sheets

TEMPORARY TATTOO

CROSS REFERENCE TO RELATED APPLICATION

This application claims the benefit of U.S. Provisional Patent Application Ser. No. 62/259,286, entitled "TEMPORARY TATTOO," filed Nov. 24, 2015.

BACKGROUND OF THE INVENTION

1. Field of the Invention

The present invention relates to a temporary tattoo. More particularly, the present invention relates to a temporary tattoo for application to the hair of an individual.

2. Description of the Related Art

Tattoos have been used for many years, but have become more prevalent in today's society. A tattoo is typically applied to an individual's skin with tattoo needles and becomes permanent. Not everyone desires a permanent tattoo so temporary tattoos have become a common trend among young adults and children as a means of self-expression. Although tattoos are typically applied to the skin of an individual, Applicant desires to create a temporary tattoo which can be applied to either the skin or hair of an individual.

SUMMARY OF THE INVENTION

It is, therefore, an object of the present invention to provide an image transfer sheet for producing a temporary tattoo including a base release sheet and a tattoo image formed on the base release sheet, the tattoo image comprising an image layer composed of a permanent adhesive and a water soluble adhesive having one or more inks integrated therewith. Wherein, after the tattoo image has been applied to a user and then subjected to water, the water soluble adhesive breaks apart and the permanent adhesive no longer has the ability to bond thereby allowing the tattoo image to easily be removed from the user.

It is also an object of the present invention to provide an image transfer sheet for producing a temporary tattoo wherein the one or more inks is mixed with the permanent adhesive and the water soluble adhesive.

It is another object of the present invention to provide an image transfer sheet for producing a temporary tattoo wherein the one or more inks is applied to the permanent adhesive and the water soluble adhesive.

It is a further object of the present invention to provide an image transfer sheet for producing a temporary tattoo wherein the base release sheet is a plastic film coated with silicone.

It is also an object of the present invention to provide an image transfer sheet for producing a temporary tattoo wherein the base release sheet is a paper sheet coated with silicone.

It is another object of the present invention to provide an image transfer sheet for producing a temporary tattoo wherein the permanent adhesive ranges between 60-80% by weight of the image layer and the water soluble adhesive ranges between 20-40% by weight of the image layer.

It is a further object of the present invention to provide an image transfer sheet for producing a temporary tattoo wherein the one or more inks is printed onto the permanent adhesive and the water soluble adhesive.

It is also an object of the present invention to provide an image transfer sheet for producing a temporary tattoo a base release sheet and an adhesive layer composed of a mixture of permanent adhesive and water soluble adhesive formed on the base release sheet. A tattoo image in the form of one or more inks is applied to the adhesive layer. Wherein, after the tattoo image has been applied to a user and then subjected to water, the water soluble adhesive breaks apart and the permanent adhesive no longer has the ability to bond thereby allowing the tattoo image to easily be removed from the user.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
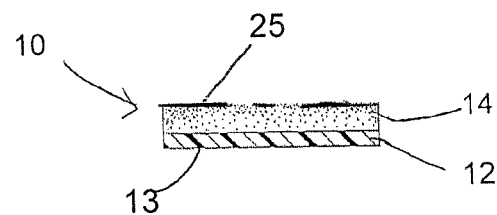
FIG. 1 is a cross-sectional view of the image transfer sheet in accordance with a first embodiment of the present invention.
Figure 2:
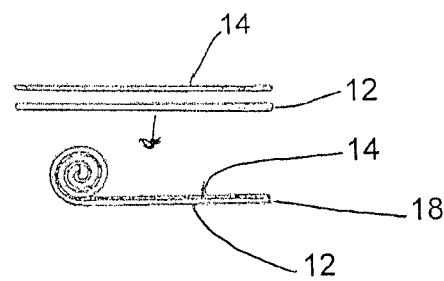
FIG. 2 is a side view showing the present invention being formed into a roll so as to be dispensed like a roll of tape.
Figure 3:
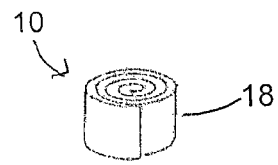
FIG. 3 shows the present invention in its rolled state.

With reference to FIGS. 1 to 3, an image transfer sheet 10 for producing a temporary hair tattoo 30 in accordance with a first embodiment is shown. The image transfer sheet 10 is particularly adapted to transfer a durable and colored image 25 to the hair or body of an individual desiring to add the selected image to his or her hair or body to function as a tattoo 30.

The image transfer sheet 10 comprises a base release sheet 12 upon which is applied the image 25 for transfer to the hair or body. In accordance with a preferred embodiment, the base release sheet 12 is a paper sheet coated with a release layer of silicone. It is also contemplated that the base release sheet 12 could be a plastic film coated with silicone, organosilcone compounds or any material that allows the release sheet to easily be removed from an adhesive, such as polypropylene, polyethylene, polyethylene terephthalate. The base release sheet 12 is between 0.1 mil to 2.0 mil, (mil=a thousandth of an inch).

As to the image 25 formed upon the base release sheet 12, it is composed of partially permanent/partially water soluble adhesive with inks (either dye and/or pigment inks) integrated therewith to form an adhesive/ink composite 14. The water soluble adhesive portion of the partially permanent/partially water soluble adhesive is selected to allow the permanent adhesive portion of the partially permanent/partially water soluble adhesive to function as a pressure sensitive adhesive, but allow the tattoo to break apart when exposed to water. As such, the image 25 is a multi-part system composed of a water soluble adhesive ranging from 20-40% by weight, a permanent adhesive ranging from 60-80% by weight, and an ink to form a printable partially permanent/partially water soluble adhesive (that is, adhesive/ink composite 14) the of the present invention. As will be appreciated based upon the following disclosure, the water soluble adhesive and the permanent adhesive combine to form a partially permanent/partially water soluble adhesive that functions as a delivery vehicle for the ink(s), so as to selectively impart a tattoo design to the hair or body of an individual. The image 25 is formed by printing the adhesive/ink composite 14 onto the base release sheet 12 via flexographic or gravure printing.

The water soluble adhesive is preferably a vinyl acetate homopolymer, in particular Accubond 4-0171, but other water soluble adhesives could be used. As those skilled in the art will certainly appreciate, vinyl acetate homopolymers include polymers of all molecular weights formed from the free radical polymerization of vinyl acetate monomer.

The permanent adhesive is preferably a water-insoluble pressure sensitive adhesive (PSA), in particular Prosaid by Adm Tronics, Inc. (PSR 300 Ominova). As those skilled in the art will appreciate PSAs are adhesives which form a bond when pressure is applied to marry the adhesive with the surface to which it is to be adhered. No solvent, water, or heat is needed to activate the adhesive. In accordance with a preferred embodiment of the present invention, the PSA may be composed of acrylic, styrene acrylic, ethylene vinyl acetate polyurethane or rubber urethane.

In accordance with a first embodiment, the adhesive/ink composite 14 is applied to the base release sheet 12 (with the ink being previously integrated into the partially permanent/partially water soluble adhesive) to create the desired image 25. The adhesive/ink composite 14 forms a layer which is between 0.1 mil to 2.0 mil thick. The water soluble adhesive and the permanent adhesive are first combined and the ink is thereafter mixed to produce the adhesive/ink composite 14. The adhesive/ink composite 14 is then applied to the base release sheet 12 in a desired pattern in accordance with the specific image 25. Such an application process is preferred where the image 25 has a single color.

As shown in FIG. 2, after the adhesive/ink composite 14 is printed onto the base release sheet 12 a web 18 is formed. The web 18 formed by the combination of the adhesive/ink composite 14 and base release sheet 12 can then be rolled such that the image 25 forming the temporary tattoo 30 can be dispensed similar to a conventional roll of adhesive tape. In this embodiment the base release sheet 12 is coated on both sides with silicone to prevent the adhesive/ink composite 14 from sticking to the backside 13 of the base release sheet 12 when dispensed. It is also contemplated that the web 18 can be cut into strips or perforated at the point at which the pattern of the image 25 formed by adhesive/ink composite 14 repeats itself. The perforations will permit the web to easily be torn.

Figure 4:
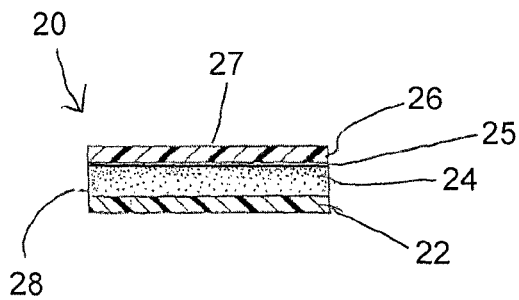
FIG. 4 is a cross-sectional view of the image transfer sheet in accordance with a second embodiment of the present invention.
Figure 5:
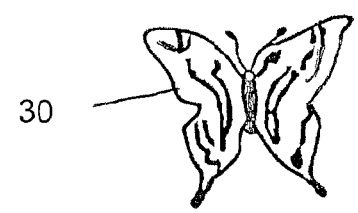
FIG. 5 shows a sample temporary tattoo in accordance with the present invention.
Figure 6:
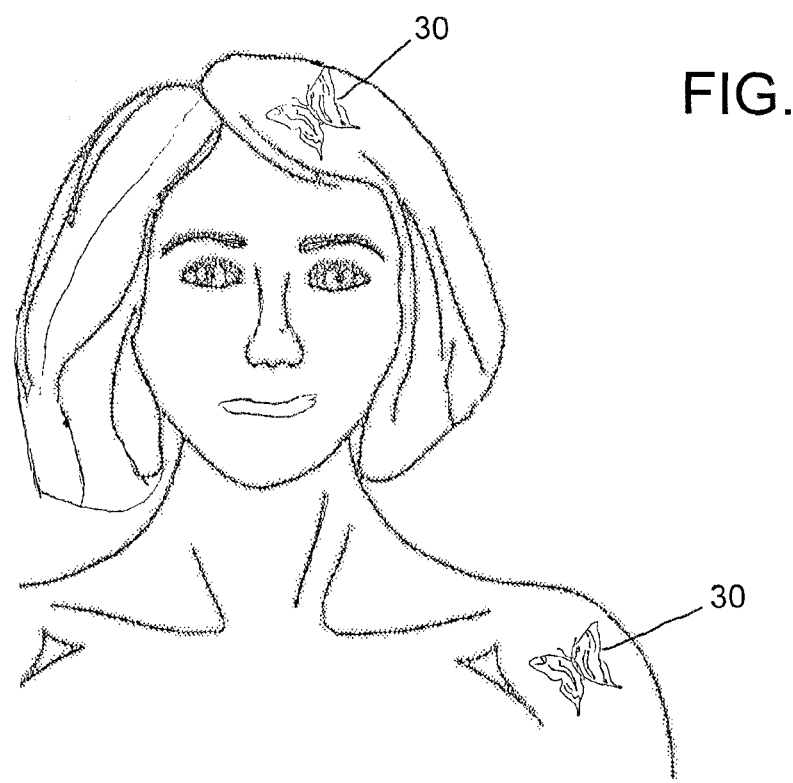
FIG. 6 shows temporary tattoos in accordance with the present invention applied to the hair of an individual.

In accordance with a second embodiment as shown in FIG. 4, the image transfer sheet 20 is formed by first mixing the water soluble adhesive and the permanent adhesive to create a partially permanent/partially water soluble adhesive. The partially permanent/partially water soluble adhesive is then applied to the base release sheet 22 as an adhesive layer 24. The adhesive layer 24 is between 0.1 mil to 2.0 mil thick. Thereafter, the ink or inks 20 are applied to the adhesive composite layer 24 in a desired pattern in accordance with the specific design set to print via flexographic or gravure printing. Such an application process is preferred where the image 25 has a multiple color.

In accordance with the second embodiment it is preferred that a Delam/Relam process be used. In accordance with such a process after the adhesive layer 24 is applied to the base release sheet 22, the adhesive layer 24 is covered by a top release sheet 26 and the sheets are laminated together to form a web 28. During the Delam/Relam process one side of the web 28, that is, the top release sheet 26 is peeled back and the ink 20 is printed onto the adhesive layer 24 as the top release sheet 26 is re-laminated back together with the adhesive layer 24 and base release sheet 22. The web 28 can then be rolled such that the image 25 forming the temporary tattoo 30 can be dispensed in a manner similar to a conventional roll of adhesive tape. Once again, it is also contemplated that the web 28 can be cut into strips or perforated at the point at which the pattern of the image 25 repeats itself.

The temporary tattoo 30 is applied to the hair or skin of an individual in the following manner. In accordance with the first embodiment, the image transfer sheet 10 is dispensed from the roll and cut to the desired length. Thereafter, and with the image 25 exposed, the base release sheet 12 of web 18 is pressed on to the hair or body at the desired location such that the exposed image 25 contacts the hair or body and the individual's hand contacts the backside 13 of the base release sheet 12. The pressure and heat from the individual's hand will cause the image 25 to release from the base release sheet 12 and adhere after about 1-2 minutes of contact. The pressure is removed and the image 25 releases from the base release sheet 12 and attaches to the individual to form a temporary tattoo 30.

If the image transfer sheet 20 includes a web 28 with two release sheets in accordance with the second embodiment, the image transfer sheet 20 is cut to the desired length. Thereafter, the image 25 is exposed by removing the base release sheet 22. With the image 25 exposed, the top release sheet 26 of web 28 is pressed onto the hair or body at the desired location such that the exposed image 25 contacts the hair or body and the individual's hand contacts the topside 27 of the top release sheet 26. The pressure and heat from the individual will cause the image 25 to release from the top release sheet 26 and adhere after about 1-2 minutes of contact. The pressure is removed and the image 25 releases from the top release sheet 26 and attaches to the individual to form a temporary tattoo 30.

When it is desired to remove the temporary tattoo 30 from the individual, water is applied. The application of water breaks down the partially permanent/partially water soluble adhesive. More particularly, due to the amount of water soluble adhesive the temporary tattoo 30 simply falls apart and the pressure sensitive adhesive no longer has the ability to bond to a surface. The temporary tattoo 30 can easily be removed from the hair by applying a sufficient amount of water, for example when taking a shower. The water will cause the water soluble adhesive to dissolve and thus the tattoo will fall apart and the permanent adhesive will no longer bond to the hair.

While the preferred embodiments have been shown and described, it will be understood that there is no intent to limit the invention by such disclosure, but rather, is intended to cover all modifications and alternate constructions falling within the spirit and scope of the invention.

The invention claimed is:
1. An image transfer sheet for producing a temporary tattoo, comprising:
   a base release sheet;

a tattoo image formed on the base release sheet, the tattoo image comprising an image layer composed of a permanent adhesive, a water soluble adhesive having one or more inks; and wherein, after the tattoo image has been applied to a user and then subjected to water, the water soluble adhesive breaks apart and the permanent adhesive no longer has the ability to bond thereby allowing the tattoo image to easily be removed from the user.

2. The image transfer sheet for producing a temporary tattoo of claim 1, wherein the base release sheet is a plastic film coated with silicone.

3. The image transfer sheet for producing a temporary tattoo of claim 1, wherein the base release sheet is a paper sheet coated with silicone.

4. The image transfer sheet for producing a temporary tattoo of claim 1, wherein the permanent adhesive ranges between 60-80% by weight of the image layer and the water soluble adhesive ranges between 20-40% by weight of the image layer.

5. An image transfer sheet for producing a temporary tattoo comprising:
a base release sheet;
an adhesive layer composed of a mixture of permanent adhesive and water soluble adhesive formed on the base release sheet;
a tattoo image in the form of one or more inks applied to the adhesive layer; and
wherein, after the tattoo image has been applied to a user and then subjected to water, the water soluble adhesive breaks apart and the permanent adhesive no longer has the ability to bond thereby allowing the tattoo image to easily be removed from the user.

6. The image transfer sheet for producing a temporary tattoo of claim 5, wherein the one or more inks is printed onto the permanent adhesive and the water soluble adhesive.

7. The image transfer sheet for producing a temporary tattoo of claim 5, wherein the base release sheet is a plastic film coated with silicone.

8. The image transfer sheet for producing a temporary tattoo of claim 5, wherein the base release sheet is a paper sheet coated with silicone.

9. The image transfer sheet for producing a temporary tattoo of claim 5, wherein the permanent adhesive ranges between 60-80% by weight of the image layer and the water soluble adhesive ranges between 20-40% by weight of the image layer.

10. The image transfer sheet for producing a temporary tattoo of claim 5, wherein the tattoo image is printed onto the adhesive layer.

* * * * *